United States Patent [19]
Ballier

[11] Patent Number: 6,030,387
[45] Date of Patent: *Feb. 29, 2000

[54] FIXING MEANS

[76] Inventor: Roland Ballier, Jagerhofstrasse 2, D-78532 Tuttlingen, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/011,924

[22] PCT Filed: May 22, 1997

[86] PCT No.: PCT/EP97/02636

§ 371 Date: Jun. 8, 1998

§ 102(e) Date: Jun. 8, 1998

[87] PCT Pub. No.: WO97/48347

PCT Pub. Date: Dec. 24, 1997

[30] Foreign Application Priority Data

Jun. 17, 1996 [DE] Germany ............... 296 10 638 U

[51] Int. Cl.[7] .................................................. A61B 17/64
[52] U.S. Cl. .......................... 606/59; 606/54; 606/104
[58] Field of Search ......................... 606/104, 53, 54, 606/56, 59, 72, 75, 96

[56] References Cited

U.S. PATENT DOCUMENTS 5,312,403  5/1994  Frigg ........................................ 606/54
5,578,032  11/1996  Lalonde .................................. 606/54

FOREIGN PATENT DOCUMENTS 41 13 083 C2  10/1992  Germany .
94 02 291  2/1994  Germany .

*Primary Examiner*—Michael Buiz
*Assistant Examiner*—David O. Reip
*Attorney, Agent, or Firm*—Kenyon & Kenyon

[57] ABSTRACT

A fixation device with clamping jaws with rods connecting the clamping jaws, said rods being adjustable axially and angularly for positioning relative to the clamping jaws and clampable in the desired position, and with fixation and retaining pins that are receivable in a clampable fashion in the clamping jaws. According to the present invention, a fixation pin applicator can be connected in a releasable fashion. A fixation pin can be brought into a desired position using of the fixation pin.

6 Claims, 3 Drawing Sheets

FIXING MEANS

FIELD OF THE INVENTION

The present invention relates to a fixation device for a bone fracture.

BACKGROUND OF THE INVENTION

A fixation device according to the species is already known from DE 41 13 083 A1. This fixation device has three or four rings as clamping jaws, said rings being designed as either closed or sector rings. The rings are connected with one another by rods. For mutual positioning of the rings, the rods are axially displaceable and pivotable with respect to the rings and can be clamped in position respective to the rings. Holders are provided on the rings for bone wires or bone fixation and retaining pins.

The known fixation device permits free relative movement of the rings in space so that the bone fragments can be positioned and repositioned very exactly. The fixation device is secured in a stable fashion in precisely set positions by clamping the rods to the rings.

A fixation device is known from DE 94 01 291 U that has only two clamping jaws for provisional emergency care of the patient, with each sector ring having two holders for the clamping pins and with each holder having at least two receptacles for the clamping pins, i.e. the fixation and retaining pins, said receptacles being offset with respect to one another perpendicularly with respect to the plane of the sector ring. The clamping pins are designed as cylindrical pins that have a small point at their anterior ends, said point being capable of being pressed superficially into the bone. These clamping pins are provided with an external thread in their rear areas. After the clamping jaws are positioned, the clamping pins are then advanced by the suitably designed receptacle that cooperates with the external threads of the clamping pins until they rest on the surface of the bone and provide the necessary grip. This fixation of the clamping pins is cumbersome and time-consuming.

SUMMARY OF THE INVENTION

An object of the present invention therefore is to improve a fixation device according to the species in such fashion that positioning and fixation of the fixation device on the bone are considerably simplified.

This object is achieved according to the invention with a fixation device with clamping jaws having rods connecting the clamping jaws, the rods being adjustable axially and angularly relative to the clamping jaws and clampable in a desired position. The fixation device includes a fixation pin applicator releasably connectable with the clamping jaws for bringing a fixation pin into a desired position.

The fixation device offers a minimally invasive alternative to surgery of fractures of the tibia. The individual fragments are secured in the area of the cortex in each instance without the medullary cavity being opened (so-called pinless nail method). The fixation device can be applied rapidly and simply because of the fixation pin applicator provided according to the invention, and permits intraoperative and postoperative repositioning in all planes. This technique avoids contamination of the medullary cavity. A direct procedural change to marrow nailing poses no risk, i.e., it can be performed without an increased risk of infection. In addition, when the fixation device according to the invention is used, the device can remain in place even during marrow nailing, considerably simplifying marrow nailing and also allowing the procedure to be performed more rapidly.

Advantageous embodiments of the present invention include that the fixation pin applicator can be designed in the form of a pistol, and can have in addition to a fixed handle, a movable handle part by which a plunger acting on the fixation pin can be displaced.

In the retaining pin applicator, a transport plate for moving the plunger against the force of a spring can be moved by the movable handle part. The plunger and therefore the retaining pin is thus moved toward the desired position by this transport plate.

The fixation pin applicator can be secured to the clamping jaw by a latching mechanism in an especially simple fashion. To release the latching mechanism, the fixation pin applicator has an externally operable release that is connected by a rod with the latching mechanism.

The fixation device can include of two clamping jaws that can be brought into the desired position with respect to one another by corresponding rods. According to one advantageous embodiment of the present invention, however, additional connecting elements can be linked to the clamping jaws, said elements having suitable clamping devices to receive additional rods and hence to connect additional clamping jaws. The fixation device can thus be expanded as desired.

The fixation and retaining pins can have different shapes. Thus, they can be made straight or bent at an angle as single pins. They can also be designed as so-called dual pins, forked pins located parallel to one another. Fixation pins can also be made spoon-shaped at their ends and provided with a plurality of points parallel to one another, and here as well they can be in the form of single or dual pins.

BRIEF DESCRIPTION OF THE DRAWINGS

Further details and advantages of the invention will now be described in greater detail with reference to an embodiment shown in the drawing.

DETAILED DESCRIPTION

Figure 1:
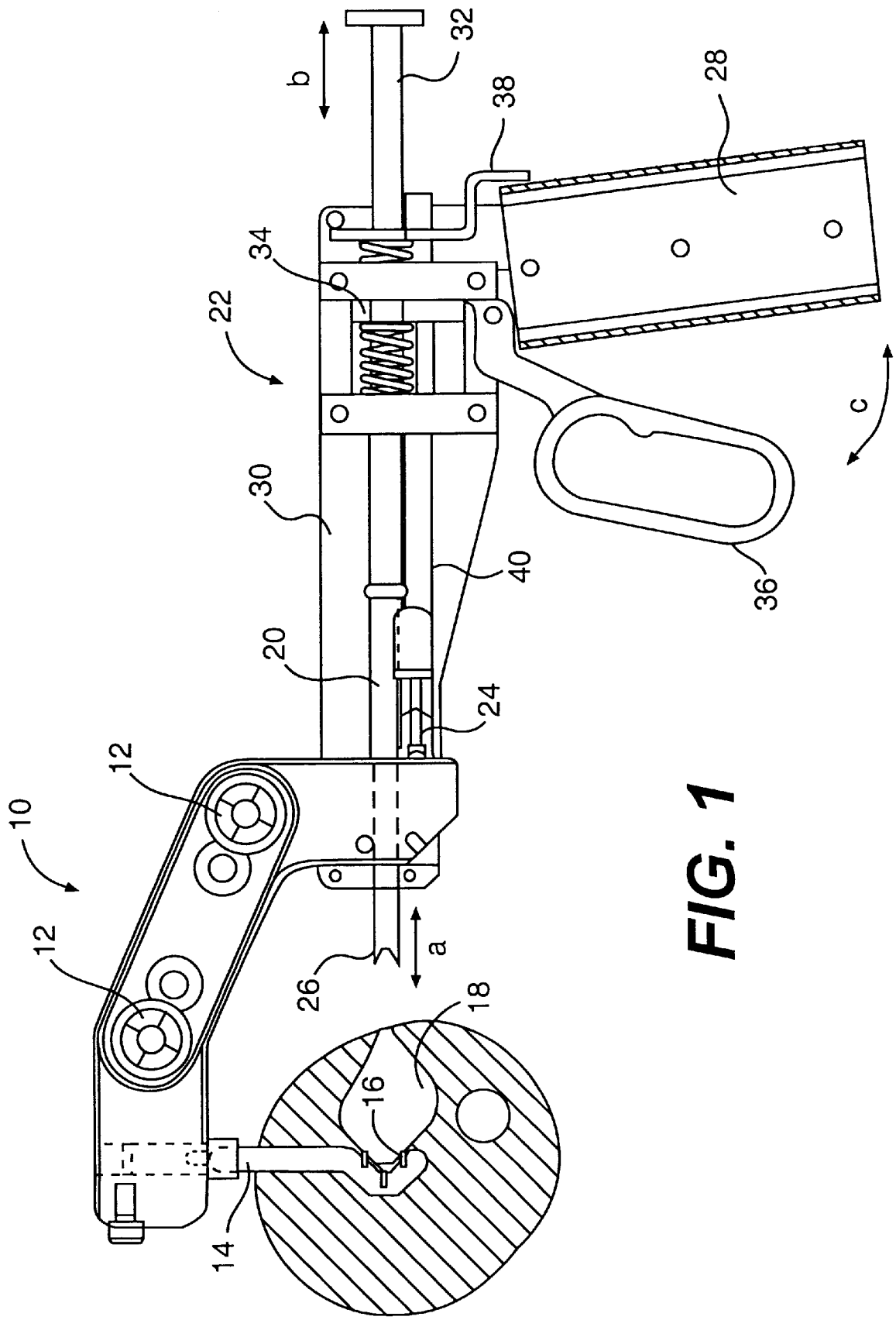
FIG. 1 is an axial plan view of the fixation device with the fixation pin applicator in place.
Figure 2:
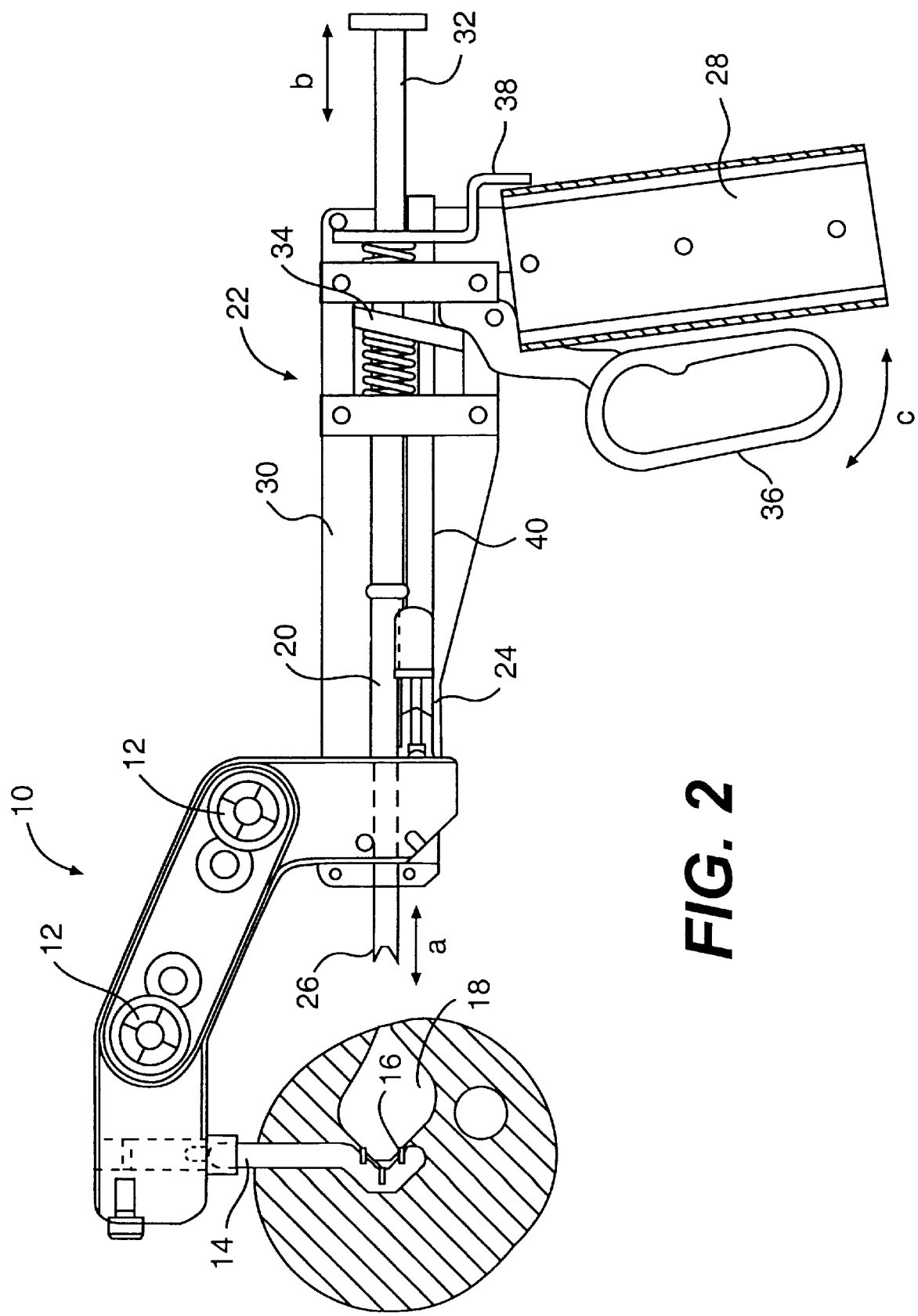
FIG. 2 is a view as in FIG. 1, with the fixation pin applicator shown in another operating position.
Figure 3:
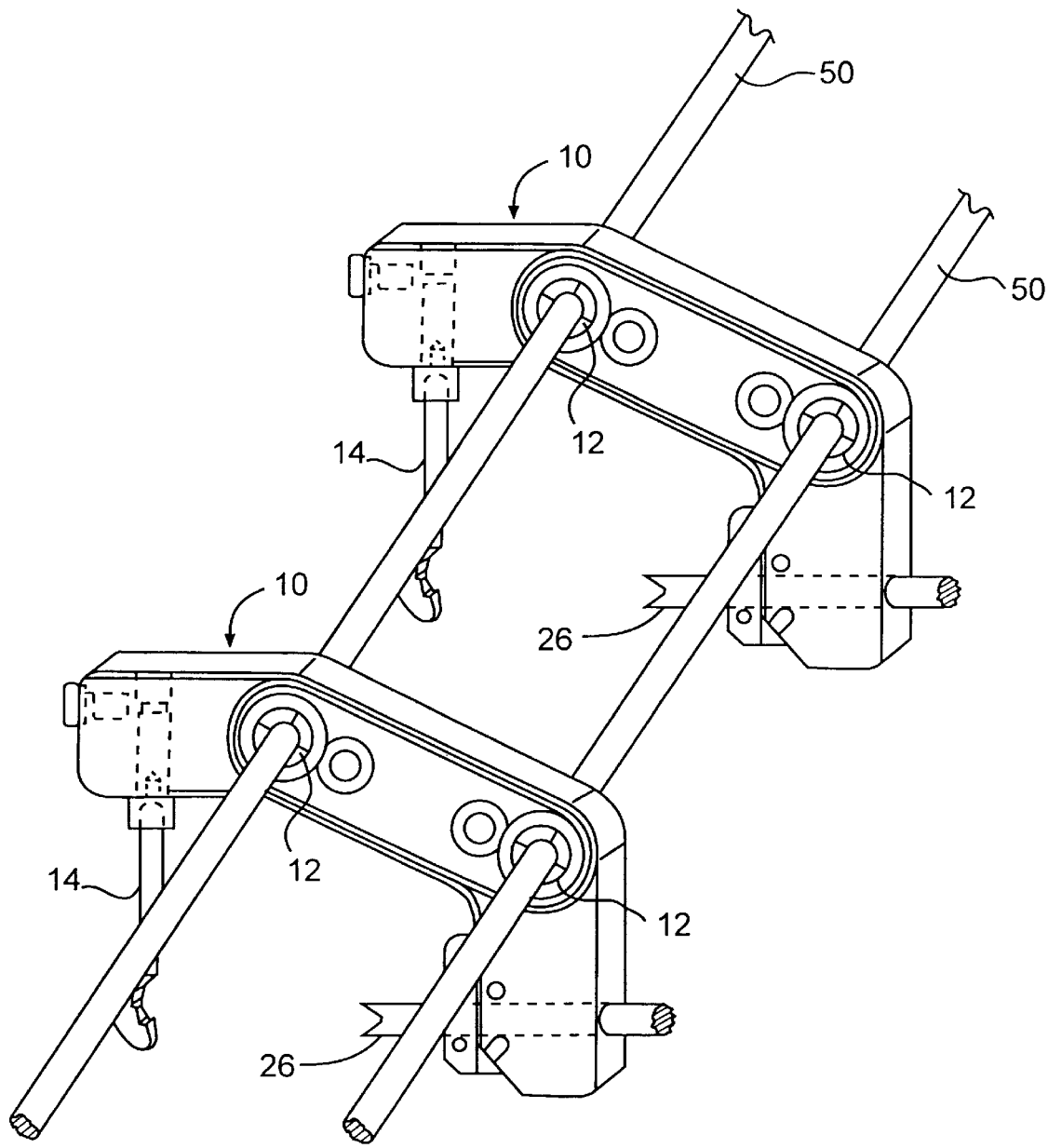
FIG. 3 is a perspective view of the fixation device clamping jaw of FIG. 1 with an additional clamping jaw.

The fixation device has a plurality of clamping jaws shown in FIG. 3, with only one such clamping jaw 10 being shown in FIGS. 1 and 2. Clamping jaws 10 in this case are formed from straight sections bent at an angle with respect to one another, but can also be formed of sector rings. Clamping jaws 10 are connected by axial rods, shown in FIG. 3. The axial rods are axially displaceable in the clamping jaws and can be pivoted relative to the plane of clamping jaws 10. As a result, free three-dimensional adjustment of clamping jaws 10 relative to one another is possible. In a given desired position, the rods can be clamped in clamping jaws 10 both axially and in their pivoted position. As a result, clamping jaws 10 are connected in stable fashion with one another in their mutual positions in space.

Clamping jaws 10 have two clamping receptacles 12 to receive rods, rods 50, shown in FIG. 3. Clamping receptacles 12 are equipped with clamping balls as described in greater detail in DE 94 02 291 U and DE 41 13 083 A, incorporated herein by reference in their entirety.

As shown and described in the drawings and text of the German '083 patent, the clamping balls have a passage that extends diametrically across the ball, and is designed to receive an axial rod. The clamping balls also have slots cut on their surface, along meridian lines. These slots allow the clamping ball to contract radially by a small amount when squeezed, so that the diameter of the passage is reduced. The specific configuration of the clamping balls is not important, as long as they allow a reduction in diameter of the passage when the clamping ball is squeezed.

The connection between the axial rods and the clamping jaw of the present invention can be fixed in a desired position by pressing a clamping plate against the jaw. This is achieved by tightening screws that hold the clamping plate to the jaw, so that movement of the rods in all axes is stopped.

The slotted balls can pivot, for example, between spherical or conical bearing surfaces. By tightening the clamping plate against the jaw, the bearing friction between the slotted balls and the bearing surfaces can be adjusted, to impede or completely prevent motion of the balls. The tightening of the clamping plate also immobilizes the rod placed in the passage of the axial balls, by reducing the diameter of the passage through the balls. The rods are thus prevented from translating and from rotating relative to the jaw.

In operation, the axial rods 50 shown in FIG. 3 are inserted in passages of the clamping balls, while the screws attaching the clamping plate to the clamping jaw are loose. Once the clamping jaw 10 is in the proper position relative to the rod, the screws are tightened, preventing further rotation of the clamping balls, and translation of the axial rods within the passage.

A retaining pin 14 can be inserted at one end of clamping jaw 10, perpendicularly to clamping jaw 10. This retaining pin 14, as shown in the embodiment illustrated here, can be designed as a so-called double-spoon pin. For this purpose, retaining pin 14 is bent at its free end so that it is spoon-shaped in cross section and has a plurality of points 16 that serve for fixation in the cortex of a tibia 18 for example.

At the opposite free end of clamping jaw 10, a fixation pin 20 is guided in an axially displaceable manner in the direction a indicated by the double arrow. For axial displaceability of fixation pin 20, in other words for positioning said pin in the cortex of tibia 18, a fixation pin applicator 22 is connected securely but releasably by a latching mechanism 24 with clamping jaw 10.

Fixation pin 20 can be positioned rapidly and simply at the desired location using fixation pin applicator 22. After fixation pin 20 has been positioned, in other words after point 26 of fixation pin 20 has engaged the cortex, said pin being V-shaped for example, fixation pin 20 is secured to the clamping jaw in any known manner that allows the two components to be connected and then released as needed. After fixation pin 20 has been secured to the clamping jaw, fixation pin applicator 22 is released from clamping jaw 10.

Fixation pin applicator 22 is designed in the shape of a pistol and has a fixed handle 28 and a housing 30 that resembles a pistol barrel. A plunger 32 is located in housing 30, said plunger being axially displaceable in the direction b indicated by the double arrow, said plunger acting on the fixation pin inserted into fixation pin applicator 22. Plunger 32 is displaceable by means of a transport plate 34. This transport plate is impacted upon by a movable handle part 36 as the movable handle part is pivoted in the direction c indicated by the double arrow. This kinematic arrangement is apparent from a comparison of FIG. 1 showing handle part 36 in its initial position and FIG. 2 showing the handle part in its pivoted position.

A release lever 38 is also mounted on fixation pin applicator 22, said lever being connected by a rod 40 with latching mechanism 24. The fixation pin applicator can be released in simple fashion from clamping jaw 10 by actuating release lever 38.

The fixation device according to the invention can be used as follows: first, clamping jaws 10 are fitted with the selected retaining pin 14. Then the fixation pin applicator is connected to the clamping jaw, with a selected fixation pin 20 being inserted. This clamping jaw, provided with pins 14 and 20, is placed over the portion of tibia 18 where implantation is to occur and the apparent perforations in the skin are marked. A lengthwise incision approximately 8 to 10 mm long is made in the skin with a scalpel, the soft tissues are scraped away using a raspatory, and the bone is exposed down to the periosteum. Then the selected fixation and retaining pins 20 and 14, together with fixation pin applicator 22 and clamping jaw 10, are introduced into the soft tissues, ideally between the bone and the raspatory, until retaining pin 14 gains a sufficient grip in the vicinity of the rear edge of the tibia. Then fixation pin 20 is introduced by means of fixation pin applicator 22 through the prepared skin incision in the area of the forward edge of the tibia until proper bone contact is achieved. The implants are finally fixed in place by multiple actuation of handle 36. A sufficient grip of clamping jaw 10 is obtained when the injured extremity can be lifted at the clamping jaw from the support without the pins tearing loose. In the same fashion, the fragment opposite the fracture is secured with one or two clamping jaws 10.

When dual pins are used, it is sufficient to connect the clamping jaws located proximally and distally with respect to the fracture by means of sufficiently long rods. The fracture is repositioned for example while being viewed on an x-ray image converter. As soon as the axes of the fragments have been aligned, final fixation of the rods is performed.

I claim:

1. A fixation device, comprising (a) a clamping jaw, (b) at least one clampable rod connecting the clamping jaw to additional clamping jaws, the rods being adjustable axially and angularly relative to the clamping and the additional clamping jaws, (c) fixation and retaining pins that can be received in a clampable fashion in the clamping jaw, and (d) a fixation pin applicator releasably connectable with the clamping jaw to position a first fixation pin of the fixation pins, the first fixation pin being movable through the clamping jaw.

2. A fixation device according to claim 1, wherein the fixation pin applicator includes a fixed handle and a movable handle part.

3. A fixation device according to claim 2, further comprising a transport plate for moving a plunger against the force of a spring.

4. A fixation device according to claim 1, wherein at least one of the fixation pin and retaining pin is forked and has two points.

5. A fixation device, comprising (a) a clamping jaw, (b) at least one clampable rod connecting the clamping jaw to additional clamping jaws, the rods being adjustable axially and angularly relative to the clamping and the additional clamping jaws, (c) fixation and retaining pins that can be received in a clampable fashion in the clamping jaw, and (d) a fixation pin applicator releasably connectable with the clamping jaw to position a first fixation pin of the fixation pins, the first fixation pin being movable through the clamping jaw, the first fixation pin being directly contactable by the fixation pin applicator.

6. A fixation device, comprising (a) a clamping jaw, (b) at least one clampable rod connecting the clamping jaw to additional clamping jaws, the rods being adjustable axially and angularly relative to the clamping and additional clamping jaws, (c) fixation and retaining pins that can be received in a clampable fashion in the clamping jaw, and (d) a fixation pin applicator releasably connectable with the clamping jaw to position a first fixation pin of the fixation pins, the first fixation pin having a longitudinal pin axis and being movable through the clamping jaw along the longitudinal pin axis.

* * * * *